United States Patent
Powell

(10) Patent No.: US 11,980,628 B2
(45) Date of Patent: May 14, 2024

(54) PROSTATE CANCER TREATMENT VIA SYNERGISTIC INHIBITION OF ARYL HYDROCARBON RECEPTOR (AHR) AND SRC

(71) Applicant: CLARK ATLANTA UNIVERSITY, INC., Atlanta, GA (US)

(72) Inventor: Joann Brooks Powell, Atlanta, GA (US)

(73) Assignee: CLARK ATLANTA UNIVERSITY, INC., Atlanta, GA (US)

( * ) Notice: Subject to any disclaimer, the term of this patent is extended or adjusted under 35 U.S.C. 154(b) by 0 days.

(21) Appl. No.: 17/459,762

(22) Filed: Aug. 27, 2021

(65) Prior Publication Data

US 2021/0393652 A1    Dec. 23, 2021

Related U.S. Application Data

(62) Division of application No. 15/831,284, filed on Dec. 4, 2017, now Pat. No. 11,103,518.

(60) Provisional application No. 62/429,654, filed on Dec. 2, 2016.

(51) Int. Cl.
| | |
|---|---|
| *A61K 31/444* | (2006.01) |
| *A61K 9/00* | (2006.01) |
| *A61K 31/08* | (2006.01) |
| *A61K 31/135* | (2006.01) |
| *A61K 31/519* | (2006.01) |
| *A61K 31/655* | (2006.01) |
| *A61K 45/06* | (2006.01) |
| *A61K 47/02* | (2006.01) |
| *A61P 35/00* | (2006.01) |

(52) U.S. Cl.
CPC .......... *A61K 31/655* (2013.01); *A61K 31/519* (2013.01); *A61P 35/00* (2018.01)

(58) Field of Classification Search
CPC ...... A61K 31/519; A61K 31/655; A61P 35/00
See application file for complete search history.

(56) References Cited

PUBLICATIONS

Frauenstein, Arch Toxicol (2015) 89:1329-1336. (Year: 2015).*
Diana Duarte et al, Current research in pharmacology and drug discovery, vol. 3, 2022, 100110. (Year: 2022).*
Asim, M. et al., "Src kinase potentiates androgen receptor transactivation function and invasion of androgen-independent prostate cancer C4-2 cells", Oncogene, 27:3596-3604, (2008).
Burich, R.A. et al., "Genistein combined polysaccharide enhances activity of docetaxel, bicalutamide and Src kinase inhibition in androgen-dependent and independent prostate cancer cell lines", BJU International, 102:1458-1466, (2008).
Chang, Y.M. et al., "Nonreceptor tyrosine kinases in prostate cancer", Neoplasia, 9(2):90-100, (2007).
Creighton, C.J., "Multiple oncogenic pathway signatures show coordinate expression patterns in human prostate tumors", PLoS One, 3:e1816, (2008).
Dasilva, J. et al., "The Neuroendocrine-Derived Peptide Parathyroid Hormone-Related Protein Promotes Prostate Cancer Cell Growth by Stabilizing the Androgen Receptor", Cancer Res, 69(18):7402-7411, ( 2009).
Dong, B. et al., "FRET analysis of protein tyrosine kinase c-Src activation mediated via aryl hydrocarbon receptor", Biochim Biophys Acta, 1810(4):427-431, (Apr. 2011).
Drake, J.M. et al., "Oncogene-specific activation of tyrosine kinase networks during prostate cancer progression", PNAS, 109(5):1643-1648, (2012).
Essam, E., "Identification of c-Src as the integral component of the cytosolic Ah receptor complex, transducing the signal of 2, 3, 7, 8-tetrachlorodibenzo-p-dioxin (TCDD) through the protein phosphorylation pathway", Biochem Pharmacol, 52:1599-1612, (1996).
Frauenstein, K. et al., "Activation of the aryl hydrocarbon receptor by the widely used Src family kinase inhibitor 4-amino-5-(4-chlorophenyl)-7-(dimethylethyl)pyrazolo[3,4-d]pyrimidine (PP2)", Arch. Toxicol., 89(8):1329-1336, (2015).
Gioeli, D. et al., "Androgen receptor phosphorylation. Regulation and Identification of the Phosphorylation Sites", J. Biol Chem., 277:29304-29314, (2002).
Gioeli, D. et al., "Stress kinase signaling regulates androgen receptor phosphorylation, transcription, and localization", Mol. Endocrinol, 20:503-515, (2006).
Guo, Z. et al., "Regulation of androgen receptor activity by tyrosine phosphorylation", Cancer Cell, 10:309-319, (2006).
Heinlein, C.A. et al., "Androgen receptor in prostate cancer", Endocr Rev, 25(2):276-308, (2004).
Kraus, S. et al., "Receptor for activated C kinase 1 (RACK1) and Src regulate the tyrosine phosphorylation and function of the androgen receptor", Cancer Res., 66(22):11047-11054, (2006).

(Continued)

*Primary Examiner* — Jean P Cornet
(74) *Attorney, Agent, or Firm* — Alston & Bird LLP

(57) ABSTRACT

Simultaneous inhibition of the aryl hydrocarbon receptor (AhR) and SRC abolishing androgen receptor (AR) signaling in prostate cancer cells is disclosed herein as an effective treatment for prostate cancer. Provided herein is a therapeutic composition that comprises an aryl hydrocarbon receptor (AhR) antagonist and an SRC inhibitor. In one embodiment, the therapeutic composition further comprises a pharmaceutical excipient. In one embodiment, the AhR antagonist is CH223191 and the SRC inhibitor is PP2 and the therapeutic composition further comprises a pharmaceutical excipient. Methods of using the therapeutic composition to treat prostate cancer or to inhibit prostate cancer cells are also disclosed.

1 Claim, 4 Drawing Sheets

Specification includes a Sequence Listing.

(56) References Cited

PUBLICATIONS

Mahajan, N.P. et al., "Activated Cdc42-associated kinase Ack1 promotes prostate cancer progression via androgen receptor tyrosine phosphorylation", PNAS, 104(20):8438-8443, (2007).
Mehta, V. et al., "Potential protective mechanisms of aryl hydrocarbon receptor (AHR) signaling in benign prostration hyperplasia", Differentiation, 82(4-5):211-219, (2011).
Ojemuyiwa, M.A. et al., "Tyrosine kinase inhibitors in the treatment of prostate cancer: taking the next step in clinical development", Expert Opin Emerg Drugs, 19(4):459-470, (2014).
Ponguta, L.A. et al., "Site-specific androgen receptor serine phosphorylation linked to epidermal growth factor-dependent growth of castration-recurrent prostate cancer", J. Biol. Chem., 283:20989-21001, (2008).
Richmond, O. et al., "The Aryl Hydrocarbon Receptor is Constitutively Active in Advanced Prostate Cancer Cells", PLoS One, 9(4):e95058, (2014).
Siegel, R. et al., "Cancer statistics", CA Cancer J. Clin., 63(1):11-30, (Feb. 2013).
Su, B. et al., "Src controls castration recurrence of CWR22 prostate cancer xenografts", Cancer Medicine, 2(6):784-792, (Dec. 2013).
Suzman, D.L. et al., "Castration-resistant prostate cancer: latest evidence and therapeutic implications", Therapeutic Advances in Medical Oncology, 6(4):167-179, (Jul. 2014).
Tatarov, O. et al., "Src family kinase activity is up-regulated in hormone-refractory prostate cancer", Clin Cancer Res, 15(10):3540-3549, (2009).
Tran, C. et al., "Inhibition of constitutive aryl hydrocarbon receptor (AhR) signaling attenuates androgen independent signaling and growth in (C4-2) prostate cancer cells", Biochem Pharmacol., 85(6):753-762 (2013).
Vlaeminck-Guillem, V. et al., "Src: marker or actor in prostate cancer aggressiveness", Frontier in Oncology, 4(222):1-22, (2014).
Wu, H-C. et al., "Derivation of androgen-independent human LNCaP prostatic cancer cell sublines: role of bone stromal cells", Int. J. Cancer, 57:406-412, (1994).
Xie, G. et al., "Src-mediated aryl hydrocarbon and epidermal growth factor receptor cross talk stimulates color cancer cell proliferation", American Journal of Physiology-Gastrointestinal and Liver Physiology, 302:G1006-G1015, (2012).
Yang, X. et al., "Constitutive regulation of CYP1B1 by the aryl hydrocarbon receptor (AhR) in pre-malignant and malignant mammary tissue", J Cell Biochem., 104:402-417, (2008).
Yu, J. et al., "Src kinase-mediates androgen receptor-dependent non-genomic activation of signaling cascade leading to endothelial nitric oxide synthase", Biochem and Biophys Res Commun, 424(3):538-543, (2012).
U.S. Appl. No. 15/831,284, filed Dec. 4, 2017, U.S. Pat. No. 11,103,518, Issued.

* cited by examiner

US 11,980,628 B2

PROSTATE CANCER TREATMENT VIA SYNERGISTIC INHIBITION OF ARYL HYDROCARBON RECEPTOR (AHR) AND SRC

CROSS-REFERENCE TO RELATED APPLICATIONS

This application is a divisional of U.S. patent application Ser. No. 15/831,284 filed on Dec. 4, 2017, which claims priority to U.S. provisional patent application Ser. No. 62/429,654 filed on Dec. 2, 2016, and entitled PROSTATE CANCER TREATMENT VIA SYNERGISTIC INHIBITION OF ARYL HYDROCARBON RECEPTOR (AHR) AND SRC, which is incorporated herein by reference.

GOVERNMENT RIGHTS

Development of the inventions described herein was at least partially funded with government support through NIH grant 2G12MD007590-29 and the U.S. government has certain rights in the invention.

REFERENCE TO SEQUENCE LISTING

This application includes an electronic sequence listing in a file named 564565SEQLST.txt, created on Aug. 26, 2021 and containing 2,211 bytes, which is hereby incorporated by reference in its entirety for all purposes.

FIELD OF THE INVENTION

The present disclosure is directed to simultaneous inhibition of Aryl Hydrocarbon Receptor (AhR) and SRC to abolish androgen receptor signaling, and methods of using AhR and SRC inhibitors to treat prostate cancer.

BACKGROUND

Prostate cancer is the second leading cause of cancer death among men in Western countries. Prostate cancer is the most commonly diagnosed cancer in men. An estimated one in six men will be diagnosed with prostate cancer and 1 in 36 will die from the disease. Such rates establish prostate cancer as one of the leading causes of all cancer-related deaths in men. Prostate cancer may be treated through a combination of surgery, radiation therapy, hormone therapy or chemotherapy. The outcomes of the treatments depend on a person's age and other health problems, as well as the extent and aggression of the cancer. Treatment of aggressive prostate cancers may involve surgery, such as radical prostatectomy, radiation therapy including brachytherapy, such as prostate brachytherapy, external beam radiation therapy, high-intensity focused ultrasound (HIFU), chemotherapy, oral chemotherapeutic drugs (temozolomide/TMZ), cryosurgery, hormonal therapy, or combination thereof. Most hormone dependent cancers become resistant to treatment after one to three years and resume growth despite hormone therapy. Regarding "hormone-refractory prostate cancer" or "androgen-independent prostate cancer," the term castration-resistant has replaced "hormone refractory" because, while they are no longer responsive to castration treatment, i.e., the reduction of available androgen/testosterone/DHT by chemical or surgical means, these cancers still show reliance upon hormones for androgen receptor activation.

The cancer chemotherapic, docetaxel, has been used as treatment for castration-resistant prostate cancer (CRPC) with a median survival benefit of 2 to 3 months. A second-line chemotherapy treatment is cabazitaxel. A combination of bevacizumab, docetaxel, thalidomide, and prednisone has also been shown to be effective in the treatment of CRPC. Immunotherapy treatment with sipuleucel-T in CRPC increases survival by 4 months. The second line hormonal therapy abiraterone increases survival by 4.6 months when compared to placebo. Enzalutamide is another second line hormonal agent with a 5-month survival advantage over placebo. Both abiraterone and enzalutamide are currently being tested in clinical trials in individuals with CRPC who have not previously received chemotherapy. Only a subset of people respond to androgen signaling blocking drugs, but certain cells with characteristics resembling stem cells remain unaffected. Therefore, the desire to improve outcomes of people with CRPC has resulted in strategies of increasing doses further or combination therapy with synergistic androgen signaling blocking agents. However, these combinations will not affect stem-like cells that do not exhibit androgen signaling. There remains a need to find better treatment for prostate cancer, especially CRPC.

SUMMARY

Provided herein is a method of treating prostate cancer in a living subject. The method comprises administering an effective amount of one or more therapeutic compositions into the living subject to reduce androgen receptor signaling in the living subject to treat prostate cancer. The one or more therapeutic compositions comprise an aryl hydrocarbon receptor (AhR) antagonist and a SRC inhibitor. In one embodiment, the living subject is a human. In one embodiment, the AhR antagonist is 2-Methyl-2H-pyrazole-3-carboxylic acid (2-methyl-4-o-tolylazo-phenyl)-amide (CH223191). In one embodiment, the SRC inhibitor is 4-Amino-5-(4-chlorophenyl)-7-(t-butyl)pyrazolo[3,4-d]pyrimidine (PP2). In one embodiment, the prostate cancer is castration resistant. In one embodiment, the living subject has prostate cancer cells and the method disclosed herein reduces the proliferation of the prostate cancer cells in the living subject by at least 80%. In one embodiment, the living subject is a human having castration resistant prostate cancer (CRPC) cells, the AhR antagonist is CH223191, the SRC inhibitor is PP2, and the method reduces the amount of CRPC cells in the living subject by at least 90%. In one embodiment, the living subject has prostate cancer cells and the method includes administering one or more therapeutic compositions into the living subject to inhibit the proliferation of the cancer cells.

Further provided is a method of inhibiting prostate cancer cells, the method including contacting the prostate cancer cells with an effective amount of one or more therapeutic compositions to reduce androgen receptor signaling in the prostate cancer cells, wherein the one or more therapeutic compositions include an aryl hydrocarbon receptor (AhR) antagonist and a SRC inhibitor. In one embodiment, the AhR antagonist is CH223191. In one embodiment, the SRC inhibitor is PP2. In one embodiment, the prostate cancer cell is castration resistant. In another embodiment, the proliferation of the prostate cancer cells is reduced by at least 80%. In yet another embodiment, the cancer cells are CRPC cells, the AhR antagonist is CH223191, the SRC inhibitor is PP2, and the method reduces the proliferation of the CRPC cells by at least 90%.

Additionally provided herein is a therapeutic composition having an aryl hydrocarbon receptor (AhR) antagonist and a SRC inhibitor. In one embodiment, the AhR antagonist is CH223191. In one embodiment, the SRC inhibitor is PP2. In one embodiment, the AhR antagonist is CH223191 and the SRC inhibitor is PP2. In one embodiment, the therapeutic composition includes a pharmaceutical excipient. In one embodiment, the AhR antagonist is CH223191 and the SRC inhibitor is PP2 and the therapeutic composition further having a pharmaceutical excipient.

BRIEF DESCRIPTION OF THE DRAWINGS

The drawing figures are not necessarily to scale and certain features may be shown exaggerated in scale or in a somewhat generalized or schematic form in the interest of clarity and conciseness. For more complete understanding of the features and advantages of the present invention, reference is now made to the detailed description of the invention along with the accompanying figures, wherein.

Figure 1A:
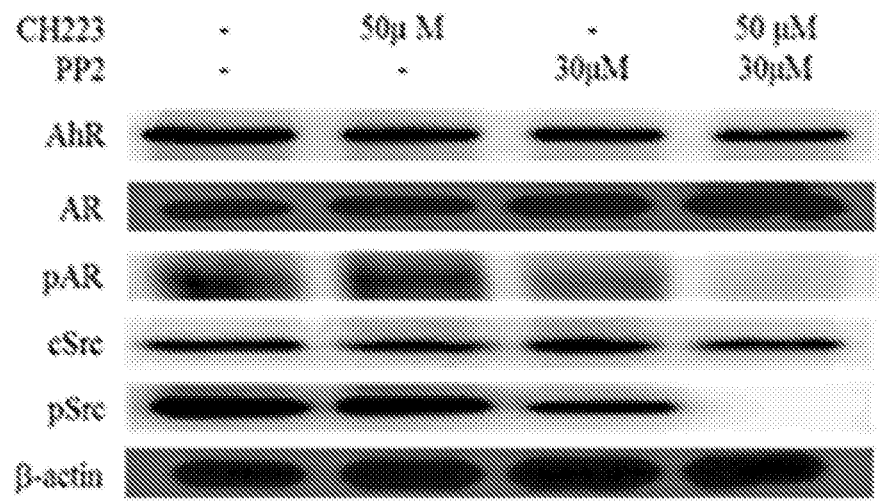
FIG. 1A shows SDS polyacrylamine gel electrophoresis results of total cellular proteins of C4-2 prostate cancer cells treated with CH223191 and PP2, alone and in combination, with DMSO as a vehicle control.

In the Figures, CH223191 was abbreviated to CH223 for formatting purposes.

DETAILED DESCRIPTION

Definitions

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may, but need not, be substituted with "within [a percentage] of" what is specified, where the percentage includes, for example, any of 0.1, 1, 5, and 10 percent.

The feature or features of any embodiment described herein may be applied to other embodiments, even though not described or illustrated expressly together, unless expressly prohibited by this disclosure or the nature of the embodiments.

As used throughout, by a "subject" is meant a living being. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In some embodiments, the subject is a mammal, such as a primate, for example, a human.

"Amount effective" and "effective amount," in the context of a composition or dosage form for administration to a subject, refers to an amount of the composition or dosage form that produces one or more desired responses in the subject, for example, preventing proliferation of prostate cancer in patients. Therefore, in some embodiments, an amount effective is any amount of a composition provided herein that produces one or more of these desired responses. The amount is one that a clinician believes to have a clinical benefit for a prostate cancer subject in need of cancer prevention or treatment.

Effective amount can involve only improving the patient's condition, although in some embodiments, it involves restoring patient's condition. An amount that is effective can also be an amount of a composition provided herein that produces a desired therapeutic endpoint or a desired therapeutic result. Administration to a subject of an effective amount of the compositions disclosed herein results in cancer treatment or prevention in the subject. The achievement of any of the foregoing are monitored by routine methods.

In various embodiments of the compositions and methods provided, the effective amount is one in which the subject is symptom-free, such as cancer-free, for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer. In other embodiments of compositions and methods provided, the effective amount is one which produces a measurable desired response, for example, a measurable decrease or disappearance of cancer in the patient for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer.

An effective amount can depend on the particular subject being treated; the severity of a condition, disease or disorder; the individual patient parameters including age, physical condition, size and weight; the duration of the treatment; the nature of concurrent therapy (if any); the specific route of administration, other conditions or diseases that the subject may have, and like factors within the knowledge and expertise of the health practitioner.

The effective amount of an aryl hydrocarbon receptor (AhR) antagonist in the therapeutic composition can be, for example, 0.1-500 mg per kg of a living subject, 0.1-1 mg/kg, 1-5 mg/kg, 6-10 mg/kg, 11-20 mg/kg, 21-30 mg/kg, 31-40 mg/kg, 41-50 mg/kg, 51-60 mg/kg, 61-70 mg/kg, 71-80 mg/kg, 81-90 mg/kg, 91-100 mg/kg, 101-110 mg/kg, 111-120 mg/kg, 121-130 mg/kg, 131-140 mg/kg, 141-150 mg/kg, 151-160 mg/kg, 161-170 mg/kg, 171-180 mg/kg, 181-200 mg/kg, 201-225 mg/kg, 226-250 mg/kg, 251-275 mg/kg, 276-300 mg/kg, 301-325 mg/kg, 326-350 mg/kg, 351-375 mg/kg, 375-400 mg/kg, 401-425 mg/kg, 426-450 mg/kg, 451-475 mg/kg, 476-500 mg/kg, 0.2-400 mg/kg, 0.5-300 mg/kg, 1-250 mg/kg, 2-200 mg/kg, 5-150 mg/kg, 10-100 mg/kg, 20-80 mg/kg, 30-70 mg/kg, 40-60 mg/kg, or 45-65 mg/kg.

The reduction of proliferation of the prostate cancer cells disclosed herein means that at least 50% of the prostate cancer cells in a living subject has been abolished, for example, 50-52.5%, 52.5-55%, 52.5-57.5%, 57.5-60%, 60-62.5%, 62.5-65%, 65-67.5%, 67.5-70%, 70-72.5%, 72.5-75%, 75-77.5%, 77.5-80%, 80-82.5%, 82.5-85%, 85-87.5%, 87.5-90%, 90-92.5%, 92.5-95%, 95-97.5%, 97.5-99%, 99-99.5%, or 99.5-100%.

The predetermined interval to effect chronical treatment results can mean, for example, every day to every year, every two days, every three days, every four days, every five days, every six days, every week, every 1.5 week, every two weeks, every 2.5 weeks, every three weeks, every 3.5 weeks, every 4 weeks, every 5 weeks, every 6 weeks, every 7 weeks, every 8 weeks, every 9 weeks, every 10 weeks, every 11 weeks, every 12 weeks, every 13 weeks, every 14 weeks, every 15 weeks, every 16 weeks, every 17 weeks, every 18 weeks, every 19 weeks, every 20 weeks, every 21 weeks, every 22 weeks, every 23 weeks, every 24 weeks, every 25 weeks, every 26 weeks, every 27 weeks, every 28 weeks, every 29 weeks, every 30 weeks, every 31 weeks, every 32 weeks, every 33 weeks, every 34 weeks, every 35 weeks, every 36 weeks, every 37 weeks, every 38 weeks, every 39 weeks, every 40 weeks, every 41 weeks, every 42 weeks, every 43 weeks, every 44 weeks, every 45 weeks, every 46 weeks, every 47 weeks, every 48 weeks, every 49 weeks, every 50 weeks, every 51 week, or every 52 weeks.

"Dosage form" means a pharmacologically and/or immunologically active material in a medium, carrier, vehicle, or device suitable for administration to a subject.

"Pharmaceutically acceptable excipient", or varients thereof (e.g., 'pharmaceutically excipient") means a pharmacologically inactive material used together with the liposomes disclosed herein and carriers to formulate the compositions disclosed herein. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers.

Throughout this application, various publications are referenced. Reference to the publications is not made to indicate that applicant finds the entire contents thereof, accurate, but because at least some of the publications describe aspects of relevant state of the art.

The present disclosure may be understood more readily by reference to the following detailed description of embodiments including further reference to the Figures.

General

Altered c-SRC activity has been implicated in the development, growth, progression, and metastasis of human cancers including prostate cancer. SRC is known to regulate several biological functions of tumor cells, including proliferation. There are several SRC inhibitors under evaluation for clinical effectiveness, but they have shown little activity in monotherapy trials of solid tumors. Combination studies are being explored by in vitro analysis and in clinical trials.

Simultaneous inhibition of the aryl hydrocarbon receptor (AhR) and the SRC abolishing androgen receptor (AR) signaling in prostate cancer cells is disclosed herein as an effective treatment for prostate cancer. AhR has been reported to interact with the SRC signaling pathway during prostate cancer development. The c-SRC protein kinase is associated with the AhR complex in the cytosol and upon ligand binding to AhR, c-SRC is activated and released from the complex. AhR has also been shown to regulate AR signaling, which remains functionally important in the development and progression of prostate cancer.

Co-inhibition of AhR and SRC is shown herein to inhibit AR activity. Evaluation of total protein and cellular fractions revealed decreased pAR expression and AR nuclear localization. Assays utilizing and androgen responsive element (ARE) and qRT-PCR analysis of AR genes revealed decreased AR DNA binding and transcriptional activity in the presence of both AhR and SRC inhibitors. Furthermore, co-inhibition of AhR and SRC reduced the growth of prostate cancer cells compared to individual treatments. However, the present disclosure is the first to disclose simultaneous inhibition of AhR and SRC to inhibit AR signaling and prostate cancer cell growth.

The SRC-family tyrosine kinases (SFKs) are oncogenic enzymes that contribute to the initiation and progression of many types of cancer, including prostate cancer. SRC plays an important role in cell proliferation, differentiation, adhesion, and migration. SRC has been identified as a potent and specific therapeutic target for prostate cancer progression.

During progression to an androgen-independent state, prostate cancer cells continue to express the androgen receptor (AR) and androgen-regulated genes, indicating that the AR is critical for the proliferation of castration-resistant prostate cancer (CRPC) cells. CPRC is defined by rising prostate-specific antigen (PSA) levels or progressive disease in the setting of serum testosterone levels within the castrate range. CRPC appears to continue to rely on the AR for growth and progression.

AR is a member of the steroid hormone receptor family which is primarily responsible for mediating the physiological effects of androgens by binding to specific DNA sequences, known as androgen response elements (AREs). The AR protein is phosphorylated at multiple serine/threonine residues and phosphorylation at some of these sites has been purported to regulate nuclear localization and export. Tyrosine phosphorylation of AR protein by non-receptor tyrosine kinases SRC may have a role in AR activation in the low androgen environment, thereby promoting the development of CRPC. SRC-mediated phosphorylation of AR at Y534 resulted in the activation of AR and nuclear translocation and DNA binding in the absence of androgen.

Moreover, SRC has also been reported to interact with other pathways, such as the aryl hydrocarbon receptor (AhR) signaling pathway during prostate development. The c-SRC protein kinase is associated specifically with the AhR complex along with hsp90 in the cytosol and, following ligand binding to the Ah-receptor sub-unit, c-SRC is activated and released from the complex. AhR is constitutively active in advanced prostate cancer cell lines that model CRPC and where SRC activity is also elevated. AhR helps to sustain androgen-independent growth of prostate cancer cells. Attenuation of AhR activity reduces expression of phosphorylated AR, androgen responsive genes and androgen mediated growth. Rapid activation of c-SRC kinase following treatment with an AhR ligand has been reported in several different cell lines and may be required for AhR mediated regulation of AR activity.

SRC is highly expressed in PCa cell lines, as well as in the majority of PCa specimens. SRC inhibitors have recently reached the clinical development stage in managing patients with metastatic PCa. However, SRC inhibitors have shown little activity in monotherapy trials and combination studies are being conducted to further evaluate the effect of SRC inhibition solid tumors. The importance of c-SRC kinase activity for aryl hydrocarbon receptor (AhR) signaling has been demonstrated and may identify AhR as a target in combination therapy. Disclosed herein are compositions and methods of co-targeting AhR and SRC as an effective strategy to abolish uncontrolled AR activity in CRPC.

Tyrosine kinase inhibitors (TKIs) have been extensively studied as a treatment for multiple malignancies. SRC is one of the TKIs regarded as a scaffolding adaptor between membranes and/or intracellular proteins and these interactions can result in mutual activation/repression depending on phosphorylation exchanges. SRC activation has been observed in several cancers, including PCa. Through both direct and indirect interaction with the AR, SRC is able to reinforce the proliferative and antiapoptotic actions of the AR, even in the absence of specific ligands. These molecular mechanisms constitute a solid rationale in favor of the use of SRC inhibitors in routinely managing patients with PCa. However, monotherapy designed clinical trials using SRC inhibitors have had limited success and combination therapy may prove more beneficial.

Considering SRC is an integral component of the cytosolic AhR complex, AhR activity may lead to persistent phosphorylation of AR by SRC kinase even in the presence of SRC inhibitors. Co-immunoprecipitation experiments revealed that AhR forms a protein complex with SRC and regulates activity by phosphorylating SRC (Tyr416) and dephosphorylating SRC (Tyr527).

Immunoprecipitation assays revealed the association of AR with SRC, suggesting complex formation among them. Other studies have shown that SRC kinase can cause AR transactivation in C4-2 PCa cells. Inhibition of SRC kinase function with a specific inhibitor resulted in decreased AR activation. There is previous evidence that SRC can facilitate crosstalk between AhR and other transcription factors. Studies have demonstrated SRC mediated crosstalk between AhR and epidermal growth factor receptor in colon cancer cells.

The precise molecular mechanism utilized by constitutive AhR signaling to activate AR signaling requires further investigation.

As disclosed herein, co-inhibition of SRC and AhR represses AR function in a synergistic manner. Co-inhibition of AhR and SRC with CH223191 and PP2 respectively inhibited AR phosphorylation and nuclear localization. This inhibition resulted in decreased AR transcriptional activity as evidenced by a significant decrease in the activity of an androgen responsive element luciferase assay and expression of androgen responsive genes. Consequently, growth of CRPC cell line, C4-2, was significantly inhibited by co-targeting AhR and SRC when compared to individual inhibition of both pathways. AR signaling is essential for the progression of prostate cancer. Simultaneous inhibition of AhR and SRC is shown here to abolish AR signaling and decrease mortality associated with CRPC.

Inhibitors

CH-223191 is a potent and specific aryl hydrocarbon receptor (AhR) antagonist. The chemical name for CH-223191 is 1-Methyl-N-[2-methyl-4-[2-(2-methylphenyl)diazenyl] phenyl-1H-pyrazole-5-carboxamide or 2-Methyl-2H-pyrazole-3-carboxylic acid (2-methyl-4-o-tolylazo-phenyl)-amide and its structural formula is as follows.

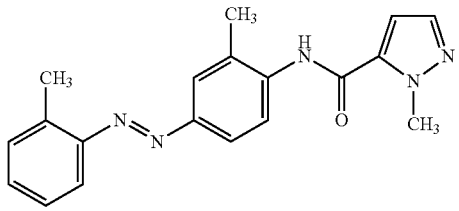 [SMILES: Cc1ccccc1/N=N/c1ccc(NC(=O)c2ccnn2C)c(C)c1]

CH-223191 inhibited TCDD-mediated nuclear translocation and DNA binding of AhR, and inhibited TCDD-induced luciferase activity with an IC50 of 30 nM. Unlike certain other AhR antagonists which display agonist activity at high concentrations, CH-223191 did not stimulate AhR-dependent transcription even at 100 micromolar. It is also specific for AhR, displaying no affinity for the estrogen receptor, as some other antagonists do.

PP2 is a selective inhibitor of SRC-family tyrosine kinases with >10,000-fold selectivity over ZAP-70 and JAK2. The chemical name for PP2 is 4-Amino-3-(4-chlorophenyl)-1-(t-butyl)-1H-pyrazolo[3,4-d]pyrimidine or 4-Amino-5-(4-chlorophenyl)-7-(t-butyl)pyrazolo[3,4-d]pyrimidine and its structural formula is as follows.

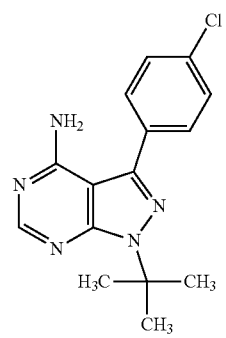 [SMILES: CC(C)(C)n1nc(-c2ccc(Cl)cc2)c2c(N)ncnc21]

Pharmaceutical Carriers/Delivery of Pharmaceutical Products

The aryl hydrocarbon receptor (AhR) antagonist and a SRC inhibitor described herein can be administered in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, and would be well known to one of skill in the art.

The compositions may be administered in any suitable way, for example, parenterally (e.g., intravenously), by intramuscular injection, by intraperitoneal injection, or the like.

The exact amount of the compositions required will vary from subject to subject, depending on the species, age, weight and general condition of the subject, the severity of the disorder being treated, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795.

The aryl hydrocarbon receptor (AhR) antagonist and a SRC inhibitor may be in solution or suspension (for example, incorporated into microparticles, liposomes, or cells).

Suitable carriers and their formulations are well known in the art. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is from about 5 to about 8, for example, from about 7 to about 7.5. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. Other compounds will be administered according to standard procedures used by those skilled in the art. Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like. The pharmaceutical composition may be administered in a number of ways depending on whether local or systemic treatment is desired, and on the area to be treated. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

EXAMPLES

Chemical and Reagents: AhR antagonist, (CH223191) was purchased from Sigma Aldrich. SRC kinase inhibitor, protein phosphatase 2 (PP2) was purchased from Sigma Aldrich.

Cell Culture: Adherent monolayer cultures of C4-2 human prostate cancer cell lines, Clark Atlanta University, Atlanta, GA, were maintained in RPMI 1640 medium supplemented with 10% FBS. Cells were grown at 37° C. with 5% CO2 in humidified atmosphere, and media was replaced every other day. Cells were split (1:3), when they reached near confluence.

Protein Isolation and Western Blot Analysis: Protein samples were isolated using the Thermo Scientific NE-PER Extraction kit for cellular fractions or commercially available cell lysis buffer (Cell Signaling) for total protein. Protein samples were resolved by SDS-PAGE and transferred to a PVDF membrane. Immunoblotting was carried out with 200 µg/ml mouse AhR monoclonal antibody at 1:500 dilution in 5% milk, 200 µg/ml mouse AR monoclonal antibody at 1:50 dilution in 5% milk, 100 µg/ml mouse pAR monoclonal antibody at 1:50 dilution in 5% milk, and 100 µg/ml rabbit pSRC monoclonal antibody at 1:1000 dilution in 5% BSA. Blots were washed three times (10 min each) with TBST. The blots were then incubated in 1:2500 dilution of secondary antibody and washed three times (15 min each) with TBS. Bands were visualized with an enhanced chemiluminescence (ECL) kit as specified by the manufacturer. Multiple exposures of each set of samples were produced. The relative concentration of target protein was determined by computer analysis using image J and normalized to an internal standard (topoisomerase, β-tubulin, β-actin).

RNA Extraction and Quantitative qRT-PCR Analysis: Total RNA was isolated from cell monolayers grown in 100 mm tissue culture dishes using RNeasy Mini Kit (Qiagen). 2 µg of the total RNA was reverse-transcribed using the Superscript II kit (Invitrogen), according to the manufacturer's recommendations. The cDNA served as a template in a 25 µl reaction mixture and was processed using the following protocol: an initial denaturation at 95° C. for 3 min, followed by 39 amplification cycles (95° C. for 10 s and 55-65° C. for 30 s), 95° C. for 10 s, 65° C. for 5 s and 95° C. for 50 s. The 25 µl qPCR reaction mixture was mixed with GoTaq qPCR Master Mix (Promega). Melt curve analyses were performed after each run to ensure a single product. Relative gene expression was determined using the ΔΔCq calculation method. The primer sequences used were:

```
CYP1B1:
Forward (5'-3')
TGCCTGTCACTATTCCTCATGCCA
&

Reverse (5'-3')
TCTGCTGGTCAGGTCCTTGTTGAT.

AhR
Forward (5'-3')
TCCTTGGCTCTGAACTCAAGCTGT
&

Reverse (5'-3')
GCTGTGGACAATTGAAAGGCACGA.

KLK3
Forward (5'-3')
ACTTCAGTGTGTGGACCTCCATGT
&

Reverse (5'-3')
AGCACACAGCATGAACTTGGTCAC.
```

-continued

AR:
Forward (5'-3')
GAGCTAGCCGCTCCAGTGCT
&

Reverse (5'-3')
CCTAACCAGGCGGGTCGTGG.

Primers to amplify the 470-bp cDNA fragment encoding L19 were used as an internal control. L-19: Forward (5'-3') TCCCAGGTTCAAGCGATTCTCCTT & Reverse (5'-3') TTGAGACCAGCCTGACCAACATGA.

Proliferation Studies: Growth of cells was assayed using the Promega CellTiter 96 Cell Proliferation Assay. Cells were resuspended to a final concentration of $1.0 \times 10^5$/mL in RPMI. 50 µl of the cell suspension (5,000 cells) was added to each well of the 96-well plate containing 50 µl of media with corresponding treatment resulting in a total volume of 100 µl. The micro plates were incubated at 37° C. for 24-72 hours in a humidified, 5% CO2 atmosphere. Per manufacturer's instructions, following incubation, 20 µl of MTS/PMS solution was added to each well and incubated for 4 hours. Absorbances were read at 490 nm using the Synergy H1m multimode micro plate reader.

Cell viability studies: Viability of cells was assayed using the Biotium XTT cell viability kit. Cells were re-suspended to a final concentration of $1.0 \times 10^5$/mL in RPMI. 100 µl of the cell suspension (10,000 cells) was added to each well of the 96-well plate. For each 96-well plate, 25 µl activation reagent was mixed with 5 ml XTT solution to derive activated XTT solution. Then 50 µl of this activated XTT was added to each well. The micro plates were incubated at 37° C. for 4 hours in a humidified, 5% CO2 atmosphere. Absorbances were read at 490 nm and 670 nm using the Synergy H1m multimode micro plate reader. Background absorbance was subtracted from signal absorbance to obtain normalized absorbance value.

XRE and ARE Binding: $4 \times 10^4$ Cells were plated in a 96 well plate. C4-2 cells were transfected with XRE and ARE reporter, as well as with positive and negative control reporter plasmids using attractene. After 16 hours of transfection, media was changed to standard assay media (DMEM+0.5% FBS+0.1 mM NEAA). Cells were grown for an additional 8 hours under normal cell conditions. After 24 hours of transfection, treat the cells and harvested cells 18 hours after treatment. A dual luciferase assay was performed after 42 hours of transfection, and promoter activity values are expressed as arbitrary florescence units (AFU). Experiments were performed in triplicate and the standard error is indicated.

Statistical Analysis: Each experiment was carried in triplicate and all the values are expressed as mean+SEM. The differences between the groups were compared by t-test or ANOVA using Instant software (GraphPad Software Inc., San Diego, CA). A value of $P<0.05$ was considered statistically significant.

Example 1

Co-Inhibition of AhR and SRC Abolishes Phosphorylation of AR

C4-2 prostate cancer cells were used as a CRPC cell model. These cells were isolated from a chimeric tumor induced by inoculating a castrated mouse with parental androgen sensitive LNCaP cells. AhR was previously reported to be constitutively active in C4-2 cells and activation of SRC kinase has been verified to accompany AhR activity. C4-2 prostate cancer cells were treated with AhR inhibitor (CH223191) and SRC kinase inhibitor (PP2) alone and in combination. DMSO served as a vehicle control. 4-amino-5-(4-chlorophenyl)-7-(dimethylethyl) pyrazolo[3,4d]pyrimidine (PP2), a widely used compound to block the activity of SRC family kinases, reduced phosphorylation of SRC and AR in C4-2 cells. Total cellular proteins were isolated and proteins were separated by SDS polyacrylamine gel electrophoresis and blotted using anti-AhR antibody, anti-AR antibody, anti-pAR antibody, anti-cSRC antibody, anti-pSRC antibody. Anti-$\beta$-actin was used as a loading control. FIG. 1 is representative of 3 independent membranes. The addition of specific AhR antagonist CH223191 abolished both SRC and AR phosphorylation in the presence of PP2. The expression levels of non-phosphorylated AR and SSRC were not affected with treatment as shown in FIG. 1A.

Figure 1B:
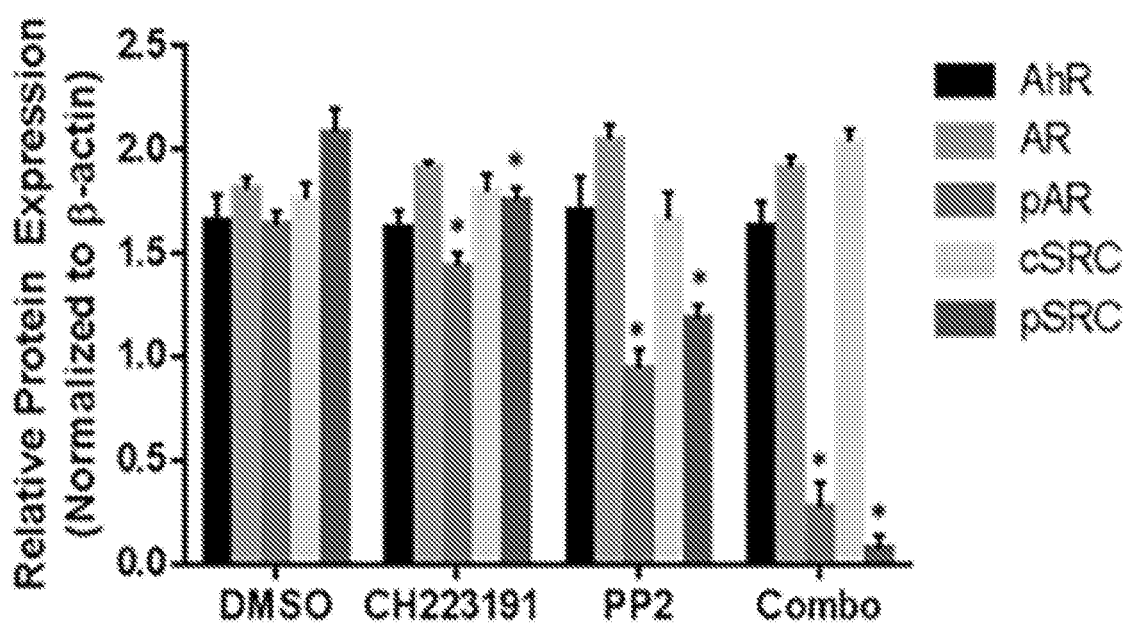
FIG. 1B shows nuclear and cytoplasmic fractionation of C4-2 cells grown on 100 mm dishes until about 75% confluent, treated with CH223191 and PP2, alone and in combination, with DMSO as a vehicle control.

Nuclear AR is AhR/SRC dependent: The translocation of AR into the nucleus is solely dependent upon the phosphorylation of AR. In order to address the role of AhR and SRC in this process, a sub-cellular localization was confirmed by immunoblotting following cellular fractionation. Nuclear and cytoplasmic fractionation: C4-2 cells grown on 100 mm dishes until ~75% confluent were treated with DMSO, CH223 and PP2 as described above. Cells were washed with cold PBS and cellular fractions were isolated per manufactures instructions using a NE-PER Extraction kit. The nuclear and cytoplasmic fractions were analyzed by western blotting for AhR and AR protein expression. The relative level of cytoplasmic AhR & AR were normalized with $\beta$-tubulin expression and the relative level of nuclear AhR & AR were normalized with topoisomerase expression. Blots are representative of three independent experiments. Individually, PP2 and CH223191 reduced the presence of AR in the nucleus with a greater effect shown with PP2. However, simultaneous inhibition of AhR and SRC abolished AR nuclear localization is shown in FIG. 1B.

Example 2

Co-Inhibition of AhR and SRC Decreases Promoter Activity of AhR and AR

Figure 2A:
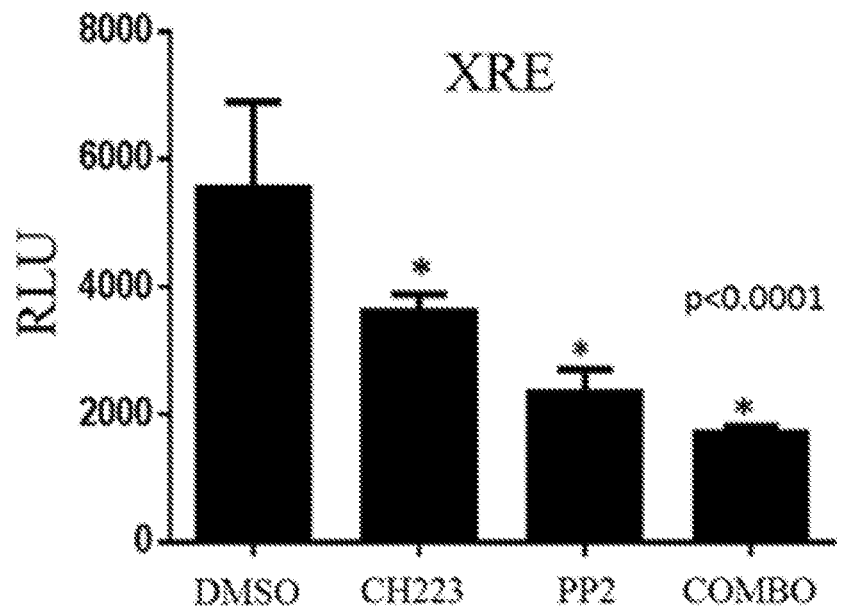
FIG. 2A shows relative light units (RLU) of C4-2 cells transfected with an XRE reporter plasmid, treated with CH223191 and PP2, alone and in combination, with DMSO as a vehicle control.
Figure 2B:
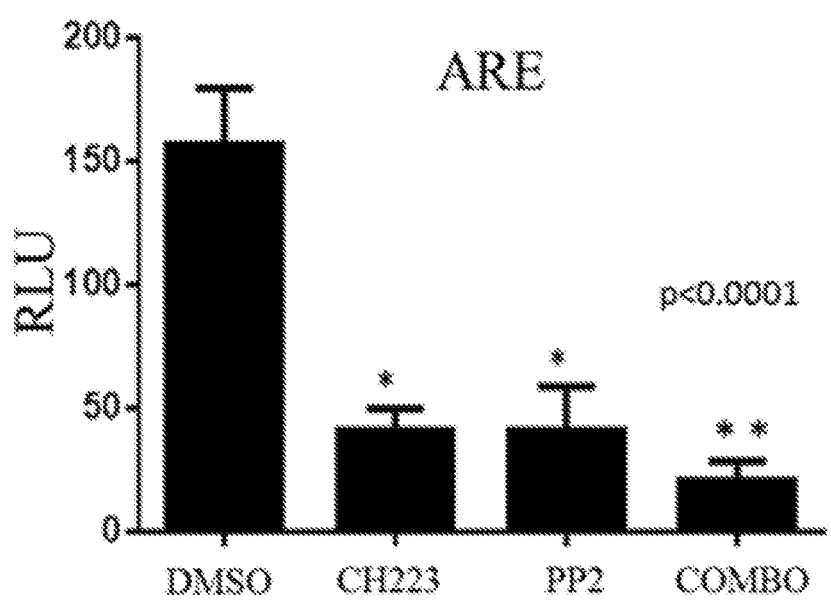
FIG. 2B shows relative light units (RLU) of C4-2 cells transfected with an ARE reporter plasmid treated with CH223191 and PP2 alone and in combination, with DMSO as a vehicle control.
Figure 3A:
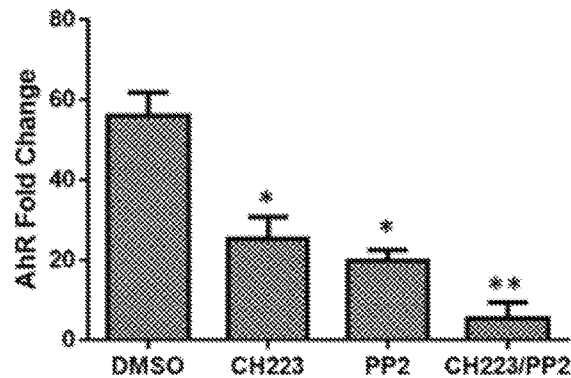
FIG. 3A shows qRT-PCR analysis of AhR mRNA expression in C4-2 prostate cancer cells treated with CH223191 and PP2, alone and in combination, with DMSO as a vehicle control.
Figure 3B:
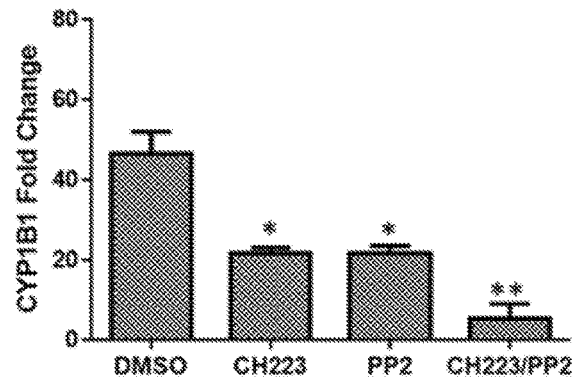
FIG. 3B shows qRT-PCR analysis of CYP1B1 mRNA expression in C4-2 prostate cancer cells treated with CH223191 and PP2, alone and in combination, with DMSO as a vehicle control.
Figure 3C:
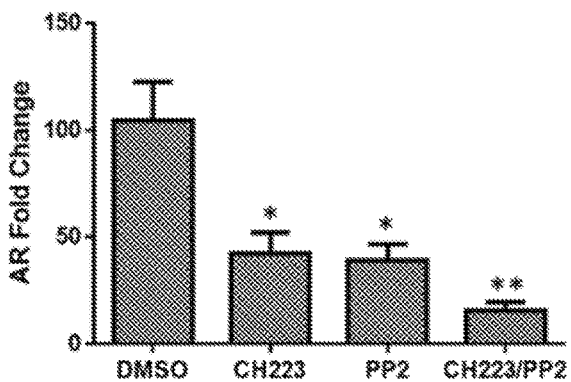
FIG. 3C shows qRT-PCR analysis of AR mRNA expression in C4-2 prostate cancer cells treated with CH223191 and PP2, alone and in combination, with DMSO as a vehicle control.
Figure 3D:
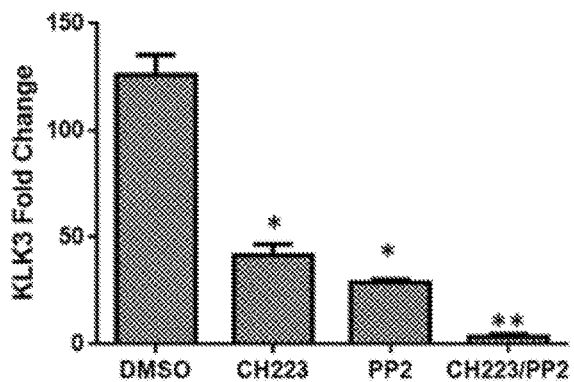
FIG. 3D shows qRT-PCR analysis of KLK3 mRNA expression in C4-2 prostate cancer cells treated with CH223191 and PP2, alone and in combination, with DMSO as a vehicle control.

The Cignal XRE and ARE luciferase reporter assays were utilized to determine the activity of AhR and AR signaling pathways in androgen independent (C4-2) prostate cancer cells in the presence and absence of inhibitors. C4-2 cells were transfected with an XRE reporter plasmid & ARE reporter plasmid, as well as with positive and negative control reporter plasmids using attractene. Following transfection, treatments were added to each appropriate plate. A dual luciferase assay was performed and promoter activity values are expressed as arbitrary florescence units (AFU). Each bar represents mean±SEM (n=3) and were analyzed by student t-test. (*) denotes statistically significant differences (*$P<0.0001$). The assay showed that C4-2 prostate cancer cells have a high level of AhR binding to XRE and of AR binding to ARE in the absence of inhibitor treatment. CH223191 reduced AhR promoter activity by 30% while PP2 resulted in a 50% decrease in XRE binding compared to DMSO. Both CH223191 and PP2 reduced AR promoter activity by 70% compared to the DMSO in ARE binding assay as shown in FIG. 2A and FIG. 2B respectively.

Simultaneous inhibition of AhR and SRC in C4-2 cells with CH223191/PP2 resulted in minimal ARE binding.

Example 3

Synergistic Inhibition of AhR and AR Target Gene Expression

To confirm the synergistic effect of CH223191 and PP2 on AhR and AR activity, qRT-PCR was used to quantify mRNA expression of AhR responsive genes (AhR and CYP1B1) and AR responsive genes (AR and KLK3) as shown in FIGS. 3A-3D respectively. qRT-PCR analysis examined AhR, CYP1B1, CYP1A1, AR, KLK2 and KLK3 mRNA expression in C4-2 prostate cancer cells. Cells were treated with 50 µM of AhR inhibitor (CH223191) or 30 µM of SRC inhibitor (PP2) alone or in combination or with vehicle control (DMSO) for 72 h and total RNAs were isolated and quantitative RT-PCR was performed to determine the mRNA expression of each target in treated cells. mRNA levels were normalized using L-19 which serves as an internal control. Each bar represents mean±SEM (n=3) and were analyzed by student t-test. (*) denotes statistically significant differences (*P<0.05) compared to control.

Since AhR is constitutively active within the C4-2 cell line, CH223191 reduced AhR and CYP1B1 gene expression more than twofold when compared to the control. While PP2 alone also decreased AhR and CYP1B1 gene expression, inhibition of gene targets was further enhanced when the cells were treated with both CH223191 and PP2. CYP1B1 gene expression was found to be very similar to the expression of AhR when treated with either CH223191 or PP2 as well when both drugs were used in combination. Elevated AhR and CYP1B1 gene expression reported before tumor formation in a rat model of mammary tumorigenesis suggested differential CYP1B1 regulation by a constitutively active AhR. CYP1B1 expression was diminished by repression of AhR activity. Because of the fundamental role of androgens in prostate development as well as prostate cancer, the objective was to determine if the effect of CH223191/PP2 also affected gene expression of AR and downstream target gene KLK3 (PSA). 50 µM of CH223191 reduced AR gene expression by 60% in C4-2 cells. An identical decrease in AR expression was observed in response to treatment with PP2. These results helped to confirm that these drugs not only decrease the expression of AhR but AR as well. Additionally, when C4-2 cells are co-treated with CH223191/PP2, AR expression is reduced by 85%. Furthermore, KLK3, which encodes for the glycoprotein prostate specific antigen (PSA), was observed to have a 65% and 70% decrease in expression in the presence of CH223191 and PP2, respectively. Yet, when these two drugs were used in combination, the level of KLK3 mRNA expression was furthered decreased to more than 97%.

Therefore, it can be concluded that these drugs have an amplified inhibitory effect on AhR and AR when used in combination.

Example 4

Figure 4A:
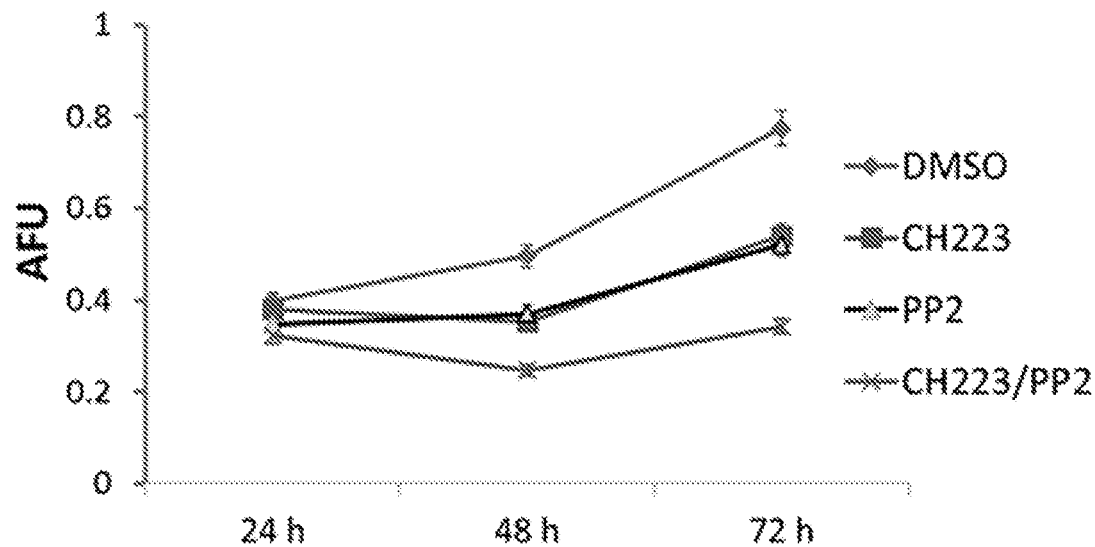
FIG. 4A shows proliferation of C4-2 prostate cancer cells treated with CH223191 and PP2, alone and in combination, with DMSO as a vehicle control.
Figure 4B:
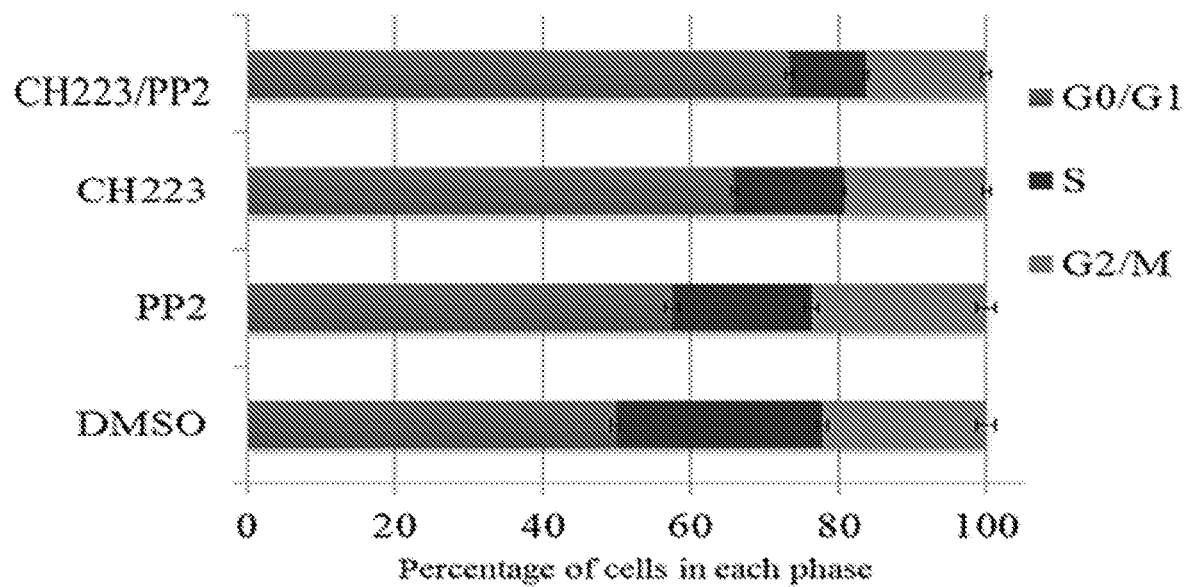
FIG. 4B shows percentage of cells from C4-2 prostate cancer cells treated with CH223191 and PP2, alone and in combination, with DMSO as a vehicle control.

Simultaneous Reduction of AhR and SRC Signaling Significantly Reduces Proliferation Expression and activity data confirmed the effectiveness of combination therapy on AR. The effects were then examined on the growth of C4-2 cells. The influence of AhR and SRC on androgen independent cell line growth was observed when C4-2 cells were grown for 24-72 hours in the presence and absence of CH223191 and PP2. CH223191 and PP2 have synergistic effect on proliferation on C4-2 prostate cancer cells. Cells were grown in a 96 well plate at 5.0×10 cells per well. The cells were treated with DMSO or 50 µM of CH223191 or 30 µM of PP2 alone or in combination for 24-72 hrs. Cell growth was measured using Promega CellTiter 96 Cell Proliferation Assay per manufacturer instructions. Each bar represents mean±SEM (n=3), *p<0.05. B.) The cells were plated at a density of 1×10 cells/dish and exposed to DMSO or 50 µM of CH223191 or 30 µM of PP2 alone or in combination for 72 hrs. Cells were harvested and analysed for cell cycle. The cells with DMSO exposure served as control. Bar graphs represent mean±SD of three separate experiments. There was no significant difference between the four treatments on the rate of growth after 24 hours exposure. The growth of C4-2 cells was significantly inhibited in the presence of CH223191 and PP2 at 48 and 72 hours. Furthermore, CH223191/PP2 demonstrated a synergistic effect on growth inhibition at 48-72 hours. After 72 hours of exposure to the combination, C4-2 cells exhibited a 50% decrease in overall growth rate compared to DMSO, as compared to a 25% decrease when CH223191 or PP2 were used alone. Together these finding demonstrate co-inhibition of AhR and SRC synergistically reduce the growth rate of C4-2 PCa cells as shown in FIG. 4A. Cell cycle analysis revealed an increase in the percent of cells in the G0/G1 phase of the cell cycle when cells were treated with either CH223191 or PP2. The percentage of cells remaining in G0/G1 was further increased when cells were co-treated with CH223191 and PP2 corresponding with the reduced growth rate seen with simultaneous inhibition of AhR and SRC as shown in FIG. 4B.

The embodiments above are intended to be illustrative and not limiting. Embodiments are within the claims. In addition, although the present disclosure has been described with reference to particular embodiments, those skilled in the art will recognize that changes can be made in form and detail without departing from the spirit and scope of the disclosure. While, as provided, publications are referenced herein to indicate aspects of the state of the art, no subject matter is incorporated that is contrary to the explicit disclosure herein.

What is claimed is:

1. A therapeutic composition, comprising 2-Methyl-2H-pyrazole-3-carboxylic acid (2-methyl-4-o-tolylazo-phenyl)-amide (CH223191) in an amount of about 50 μM and Amino-5-(4-chlorophenyl)-7-(t-butyl)pyrazolo[3,4-d]pyrimidine (PP2) in an amount of about 30 μM, and a pharmaceutical excipient.

* * * * *

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: CYP1B1 Forward
```

<400> SEQUENCE: 1
tgcctgtcac tattcctcat gcca                                          24

<210> SEQ ID NO 2
<211> LENGTH: 24
<212> TYPE: DNA
<213> ORGANISM: Artificial Sequence
<220> FEATURE:
<223> OTHER INFORMATION: CYP1B1 Reverse

<400> SEQUENCE: 2
tctgctggtc aggtccttgt tgat                                          24

<210> SEQ ID NO 3
<211> LENGTH: 24
<212> TYPE: DNA
<213> ORGANISM: Artificial Sequence
<220> FEATURE:
<223> OTHER INFORMATION: AhR forward

<400> SEQUENCE: 3
tccttggctc tgaactcaag ctgt                                          24

<210> SEQ ID NO 4
<211> LENGTH: 24
<212> TYPE: DNA
<213> ORGANISM: Artificial Sequence
<220> FEATURE:
<223> OTHER INFORMATION: AhR reverse

<400> SEQUENCE: 4
gctgtggaca attgaaaggc acga                                          24

<210> SEQ ID NO 5
<211> LENGTH: 24
<212> TYPE: DNA
<213> ORGANISM: Artificial Sequence
<220> FEATURE:
<223> OTHER INFORMATION: KLK3 Forward

<400> SEQUENCE: 5
acttcagtgt gtggacctcc atgt                                          24

<210> SEQ ID NO 6
<211> LENGTH: 24
<212> TYPE: DNA
<213> ORGANISM: Artificial Sequence
<220> FEATURE:
<223> OTHER INFORMATION: KLK3 reverse

<400> SEQUENCE: 6
agcacacagc atgaacttgg tcac                                          24

<210> SEQ ID NO 7
<211> LENGTH: 20
<212> TYPE: DNA
<213> ORGANISM: Artificial Sequence
<220> FEATURE:
<223> OTHER INFORMATION: AR forward

<400> SEQUENCE: 7
gagctagccg ctccagtgct                                               20

<210> SEQ ID NO 8

```
<211> LENGTH: 20
<212> TYPE: DNA
<213> ORGANISM: Artificial Sequence
<220> FEATURE:
<223> OTHER INFORMATION: AR reverse

<400> SEQUENCE: 8
cctaaccagg cgggtcgtgg                                               20

<210> SEQ ID NO 9
<211> LENGTH: 24
<212> TYPE: DNA
<213> ORGANISM: Artificial Sequence
<220> FEATURE:
<223> OTHER INFORMATION: L19 forward

<400> SEQUENCE: 9
tcccaggttc aagcgattct cctt                                          24

<210> SEQ ID NO 10
<211> LENGTH: 24
<212> TYPE: DNA
<213> ORGANISM: Artificial Sequence
<220> FEATURE:
<223> OTHER INFORMATION: L19 reverse

<400> SEQUENCE: 10
ttgagaccag cctgaccaac atga                                          24
```